United States Patent
Barnard et al.

(10) Patent No.: US 11,039,748 B2
(45) Date of Patent: Jun. 22, 2021

(54) SYSTEM AND METHOD FOR PREDICTIVE MODELING AND ADJUSTMENT OF BEHAVIORAL HEALTH

(71) Applicant: SYNCHRONOUS HEALTH, INC., Nashville, TN (US)

(72) Inventors: Guy Barnard, Nashville, TN (US); Lisa D. Henderson, Nashville, TN (US); Katherine A. Lohr, Nashville, TN (US)

(73) Assignee: Synchronous Health, Inc., Nashville, TN (US)

( * ) Notice: Subject to any disclaimer, the term of this patent is extended or adjusted under 35 U.S.C. 154(b) by 284 days.

(21) Appl. No.: 15/647,399

(22) Filed: Jul. 12, 2017

(65) Prior Publication Data
US 2018/0025126 A1 Jan. 25, 2018

Related U.S. Application Data

(60) Provisional application No. 62/364,358, filed on Jul. 20, 2016.

(51) Int. Cl.
*A61B 5/00* (2006.01)
*A61B 5/11* (2006.01)
(Continued)

(52) U.S. Cl.
CPC .......... *A61B 5/0022* (2013.01); *A61B 5/1113* (2013.01); *A61B 5/1118* (2013.01);
(Continued)

(58) Field of Classification Search
CPC ........ G16H 50/20; G16H 50/30; A61B 5/165; A61B 5/1118; A61B 5/0022; G06F 19/3481; G09B 19/00
See application file for complete search history.

(56) References Cited

U.S. PATENT DOCUMENTS

| 8,244,654 B1 | 8/2012 | Hobgood et al. |
| 8,473,431 B1 | 6/2013 | Mann et al. |

(Continued)

FOREIGN PATENT DOCUMENTS

WO 2017041161 A1 3/2017

OTHER PUBLICATIONS

International Search Report and Written Opinion in corresponding International Application No. PCT/US2017/042801, dated Oct. 13, 2017, 23 pp.

(Continued)

*Primary Examiner* — Jerry-Daryl Fletcher
(74) *Attorney, Agent, or Firm* — Patterson Intellectual Property Law, P.C.; Gary L. Montle

(57) ABSTRACT

A cloud-based system and method for predictive modeling and positive adjustment of behavioral health are disclosed. The system includes sensors collecting data associated with subject location and activity, and linked to a subject computing device. The system translates data aggregated from the data sources into state information, and iteratively updates, via the translated state information, a de-identified contextual model for the subject which in an embodiment may be a Life Context Graph as described herein. An end point server compares the de-identified contextual model to a de-identified aggregate of peer-based contextual models, wherein data security and privacy is preserved, and the system further iteratively updates the subject contextual model based thereon. The system accordingly identifies behavioral trigger actions based on the collected data and/or the updated subject contextual model, and generates a predetermined clinical response corresponding to the identified behavioral trigger action.

20 Claims, 5 Drawing Sheets

(51) Int. Cl.
*A61B 5/16* (2006.01)
*G16H 50/50* (2018.01)
*G16H 50/20* (2018.01)
*G16H 15/00* (2018.01)

(52) U.S. Cl.
CPC ............ *A61B 5/165* (2013.01); *A61B 5/4833* (2013.01); *A61B 5/7465* (2013.01); *G16H 50/20* (2018.01); *G16H 50/50* (2018.01); *G16H 15/00* (2018.01)

(56) References Cited

U.S. PATENT DOCUMENTS

| | | | |
|---|---|---|---|
| 8,540,515 | B2 | 9/2013 | Williams et al. |
| 8,684,742 | B2 * | 4/2014 | Siefert .................... G09B 5/10 434/236 |
| 8,768,864 | B2 | 7/2014 | Kane-Esrig |
| 2008/0001735 | A1 | 1/2008 | Tran |
| 2008/0177567 | A1 | 7/2008 | Friedlander et al. |
| 2008/0275729 | A1 | 11/2008 | Taggart et al. |
| 2010/0142692 | A1 | 6/2010 | Gotta et al. |
| 2011/0071363 | A1 | 3/2011 | Montijo et al. |
| 2011/0184250 | A1 * | 7/2011 | Schmidt ................ G16H 50/50 600/300 |
| 2012/0244504 | A1 | 9/2012 | Wasserman |
| 2013/0024211 | A1 | 1/2013 | Monteforte et al. |
| 2013/0218616 | A1 | 8/2013 | Pinchuk |
| 2013/0262357 | A1 | 10/2013 | Amarasingham et al. |
| 2014/0377727 | A1 | 12/2014 | Yom-Tov et al. |
| 2016/0055236 | A1 | 2/2016 | Frank et al. |
| 2016/0140320 | A1 * | 5/2016 | Moturu ............... G06F 19/3481 434/236 |
| 2016/0196389 | A1 | 7/2016 | Moturu et al. |

OTHER PUBLICATIONS

European Patent Office: Supplementary Search Report dated Mar. 8, 2017.

* cited by examiner

SYSTEM AND METHOD FOR PREDICTIVE MODELING AND ADJUSTMENT OF BEHAVIORAL HEALTH

CROSS-REFERENCES TO RELATED APPLICATIONS

This application claims benefit of U.S. Provisional Patent Application No. 62/364,358, filed Jul. 20, 2016, which is hereby incorporated by reference.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

An invention as disclosed herein relates generally to decision support systems for mental health services. An invention as disclosed herein may relate more particularly to the implementation of data analysis and predictive analytics to identify patterns of behavior, further optimizing the delivery of support services for subjects.

While a substantial proportion of all people will experience a mental health condition in their lifetime, a severe shortage of mental health providers can limit the availability to the help that is needed. The limited amount of time available to any individual may further be insufficient, as conventional tools such as weekly outpatient therapy frequently fail to identify and provide timely responses to the behavioral triggers and emotional responses that people go to counseling to change in the first place.

When counseling is available, it can be prohibitively expensive for individuals and for their insurance providers. Even when insurance covers the cost of mental health services, there are still deductibles and out of pocket costs, which can be thousands of dollars, not to mention the precious resource of time. For many, attending appointments is simply impractical or even impossible.

It would therefore be desirable to provide a system and method for supporting people in the exact moment they need it most, rather than at the time of the next scheduled appointment.

It would further be desirable to gather and implement real time data, and to identify triggers that would indicate a need for delivering support.

It would further be desirable to determine the effectiveness of interactions and interventions in a data-driven context, as for example each individual responds uniquely to interventions based on a complex set of factors including personality, readiness for change, genetics, family history and more.

BRIEF SUMMARY OF THE INVENTION

Exemplary systems or methods according to the present disclosure provide for the gathering, assimilation, and processing of behavioral health data pertinent to a plurality of subjects, and human-assisted artificial intelligence processing thereupon to generate an intervention-capable user interface. One exemplary purpose for generating such user interface is to understand, manage, measure, and improve the health of a given group of subjects.

In one aspect as disclosed herein, embodiments of a hosted system or method may take the form of a "conversational user interface" via a mobile application, website, or the like, existing pervasively across a network and capable of interacting with one or more subjects in response to aggregated and processed subject data. The "conversational user interface" may be the subject-facing interaction component of a larger model comprising multiple processes including surveilling patients for behavioral data and aggregating surveilled data, modeling of an individualized Life Context Graph (LCG), comparing the individualized Life Context Graph to a surrogate peer model, and providing for means for interaction and behavioral based upon trigger states obtained from the comparison.

In one aspect of the invention, the "conversational user interface" may be described as a "bot," wherein the "bot" is a healthcare decision support tool individualized to a specific subject. In an embodiment, each bot may be iteratively unique for each subject, wherein the multiple processes may be uniquely interpreted, governed, and/or applied to the subject based upon the subject's unique behavioral data and surveilled data. In various embodiments, the bot may be capable of interacting with its unique subject and one or more healthcare specialists for the subject. In an embodiment thereof, the bot may be configured to provide both voice and text feedback as well as voice and text input methods in plain language. In a further embodiment, the bots may be configured to interact and communicate with one another using the same or similar plain language communication and derive data therefrom to contribute to the aforementioned processes including surveilling patients for behavioral data and aggregating surveilled data, modeling of an individualized Life Context Graph, comparing the individualized Life Context Graph to a surrogate peer model, and providing for means for interaction and behavioral based upon trigger states obtained from the comparison.

These processes may be contemplated as individual methodologies performed iteratively and continuously in the context of the greater application for behavioral health improvement. For example, surveillance and data aggregation may generally combine traditional population health inputs with data not traditionally gathered in the context of healthcare such as employment data, personnel data, Internet of Things data, consumer behavior data, environmental data, and other such data as can be gathered from user-centric computer inputs and accounts; this data may be aggregated for an individual into a Life Context Graph representing a collection of readings, messages, entities, relationships, work items, and other things that in combination represent the context for a consumer's life, and in aggregate, that of a population. Where the process is iterative and continuous, the Life Context Graph may be updated continuously based on the ongoing introduction of new data.

In one embodiment, the Life Context Graph may be generally schema-less, being represented in any machine state by a "property dictionary" of keys and values. For example, keys may be text strings and values may be an object or sub-dictionary of keys and values, such that the introduction of new values and new keys will not invalidate prior data. As a specific example, a text string may be "[Subject] is feeling [emotion]," wherein the subject and emotion are values. In instances where the subject is "John Doe" and the emotion used to describe John Doe's emotional state is "happy," this key and value combination may be published to the Life Context Graph for John Doe as a contextual "State." Because of the schema-less nature of the string and value combination, the introduction of a new value that more specifically defines the same iteration would affect future contextual State definition without invalidating prior determinations. For example, inclusion of a new value "elated" used to describe a feeling of happiness in response to a specific trigger as opposed to a general state of contentedness may result in future States where John Does would be classified as "happy" to be now classified as "elated" without invalidating prior States in which John Doe was generally accurately classified as "happy." The Life Context Graph for John Doe would therefore grow organically based upon the introduction of new keys and values, increasing in specificity and predictive accuracy over time.

In one aspect, embodiments of a hosted system or method as disclosed herein may compare individual Life Context Graphs or States thereof with other Life Context Graphs or States thereof to create a peer group or general population model based upon the nexus of State data. The aggregation and generalization of individual Life Context Graphs into a greater population model allows for both absolute surveillance of specific subjects as well as relative surveillance of an aggregation of subjects. Population models may be constrained to certain input thresholds to create peer group models, e.g. creating a peer group of the top ten percent of the population at highest risk of depression.

One advantage of modeling peer groups and populations based on individual lifetime graphs is that comparison of individualized information can be made to de-identified data, allowing for accurate comparison of health behavioral data to health behavior models without risking data spill of other subjects. In traditional models of behavioral health model comparison, one subject is ranked against one or more other subjects to determine relative valuation. For example, John Doe might be classified as the most at risk for a behavioral state of overeating with a value of 87%, compared to Jane Smith as second-most at risk with a value of 74%, compared to Daniel Jones as third-most at risk with a value of 68%. Because these comparisons are direct, the system performing the comparison of values must have access to all three subjects' identities and data. This access creates a high risk of data spill, wherein the compromise of the system would release all three subjects' identities and healthcare data.

Comparatively, embodiments of the hosted systems and methods disclosed herein that compare individual Life Context Graphs to peer models and/or population models, the greater models can be de-identified, thereby significantly decreasing the risk of data disclosure of other peer models without sacrificing predictive and comparative accuracy. For example, hosted systems and methods may employ one or more of various privacy maintaining methods including differential privacy, homomorphic encryption, end-to-end encryption, asymmetric encryption, and shared-key encryption to transmit individual life context data to an endpoint aggregator. The endpoint aggregator may perform mathematical, statistical, and logic-based analyses to provide an assessment of the relative context of individual data against de-identified population or peer group data. Encryption tools and methodologies used herein may allow for encryption of the actual values while still allowing for application of statistical functions without direct introspection; thus, when a result of statistical analysis is decrypted, the result may be within range of the original data without revealing the specifics of the original data against which the individualized data was compared.

This methodology is novel to the healthcare and behavioral health industries. Traditionally, all population-level analytics have been performed entirely centrally, such as in a data server or cloud server with full access to population-level data. Accordingly, data comparison is done on a directly comparative basis with all information about all population members being visible to the centralized aggregator. Despite the traditional use of privacy methods such as data encryption, healthcare organizations have suffered significant data breaches and data spillage, indicating that traditional methods of data protection are insufficient. Accordingly, aforementioned de-identification methods significantly reduce risk by limiting data spillage risk to the individual consumer and their device, regardless of whether compromise occurs via the user's device or at the data aggregator level. Furthermore, the use of homomorphic encryption reduces the number of points where data compromise could occur, including at least at the aggregator, as the data does not need to be decrypted in order to perform statistical comparison.

In a further embodiment, hosted systems and methods may employ block chain tools to manage the Life Context Graph. For example, the Life Context Graph may employ block chain signatures across graph iterations or States to ensure authenticity of data in untrusted networks.

In another aspect, embodiments of a hosted system or method as disclosed herein may perform historical and predictive modeling by comparing past patterns of behavior via individualized and peer group Life Context Graphs to current behavior exhibited to determine if current behaviors are unusual and indicative in a change of risk context. Unlike traditional population health predictive models which model predictive cost, predictive death, and predictive risk in an absolute context based upon an input population, models of the systems and methods disclosed herein employ state machine methodologies to carry continuously an assessment of the risk or factors being surveilled and calculate changes in state thereupon. The state changes are therefore determined in both absolute and relative context, compared against a dynamic growth model as opposed to a static population model. In other words, the comparison of state change is performed iteratively based upon a living population as opposed to a static model of risk, allowing for more natural fluctuation of states and reducing the risk of triggering false positives.

Furthermore, unlike traditional behavioral health and healthcare models which focus on medical intervention, models disclosed herein may further include productivity outcomes, performance outcomes, total cost of living, richness of life experience, kindness, cultural contribution, and sense of community. These additional models allow for interventions for behavioral health, life experience, and kindness and thereby allow for adjustment and improvement of total well-being states and not simply medical health.

In certain embodiments, the modeling function may be recursive and feed back into the Life Context Graph as an insight, thereby permitting the Life Context Graph to be heuristic and self-learning. For example, a Life Context Graph comprised of several States showing that a subject is ambulatory, animated, posting on social media using happy contexts, near a spouse, sleeping eight hours a night, on vacation, and at a beach may result in a Life Context Graph model insight defining the subject as "happy." This model result can be fed back into the Life Context Graph as a State defining the subject as "happy." Comparative interactions with the subject or a user may accordingly adjust this State definition, such as if comparative input says that the subject is not happy and the State generation is not accurate. For example, new data in the form of additional States may redefine context, such as if modeling from the Life Context Graph determines that the subject is sunburned, and the State of being sunburned may result in a model wherein a new State says the subject is "uncomfortable" or "feeling pain" as opposed to, or in addition to, being "happy." Accordingly, the new State of being "uncomfortable" or "in pain" is added to the Life Context Graph and used for future iterations of modeling.

In yet another aspect, embodiments of a hosted system or method as disclosed herein, the modeling performed against the Life Context Graph may result in the performance of If-Then processing whereby the presence of certain States calls for the execution of certain actions. This If-Then processing of State data may be characterized herein as a WHEN-THEN or WHEN-DO programming methodology. One advantage of this type of WHEN-THEN methodology is that it permits users with very limited programming experience to define triggers and actions via simplified programming interfaces. For example, the WHEN-THEN methodology can be expressed as a visual programming language wherein trigger WHEN blocks and trigger THEN blocks can be arranged using drag and drop, pulldown, touch, and similar visual programming interfaces. Assemblies of WHEN and THEN blocks create logic flows, generally known as recipes or applications.

The combination of traditional WHEN-THEN methodology with the iterative and continuous generation and modeling of the Life Context Graph permits users to create more than simple logic flows; because of the iterative and continuous nature of the Life Context Graph and State generation, WHEN-THEN interaction creates a means by which a user can interact with the modeling process based upon triggers used from the model itself. For example, a clinical therapist user may program a flow whereby when a client subject, known to have adverse responses during thunderstorms, is sent a message action when a triggering event of a thunderstorm forecast occurs. This process allows the user to extent the user's expert empathetic behavioral care process beyond traditional scopes. The behavioral care process occurs across time, to a future unknown point at which a thunderstorm occurs, and space, to the potentially non-proximate location of the subject relative to the user.

Moreover, the WHEN-THEN methodology can be uniquely implemented in the behavioral health space via a drag-and-drop programming interface wherein IF flows are logically and visually connected to THEN actions, enabling visual interface-based programming of core logic behaviors. As opposed to having a programmer translate coach- and clinician-based diagnostics for "If-Then" responses, the deployment of a drag-and-drop interface wherein non-programmer coaches, clinicians, and other behavioral health experts allows said experts to directly and easily create the diagnostic flows necessary without relying on a third-party programmer to translate said flows. Not only does this improve accuracy and reduce errors caused by programming translations, it allows non-programmer behavioral health experts to directly extend their care iteratively and on the fly to both current need solutions and to future need solutions, improving the behavioral health modification process by enabling targeted, authentic response actions.

Because the generation of WHEN-THEN logical flows may result in the creation of multiple States fed back into the subject's Life Context Graph, iterative user interaction with the system creates a human-assisted artificial intelligence wherein human interaction can improve machine learning functions for the modeling of States. The result of this combination of methodologies allows for the implementation of highly targeted and directly actionable care and intervention actions via a behavioral care application. For example, a messaging application can identify States and actionable flows specific to the behavioral health improvement of one individual or a select group of individuals over another with minimal human assistance. For example, where a first subject may react to stress negatively and a second subject may react to stress positively, a determination of a State whereby the subject is "stressed" may result in differentiated actions based upon user-inputted flows; one flow may suggest that for subjects with positive stress reactions a message should be generated inspiring productive activity whereas another flow may suggest that for subjects with negative stress reactions a message should be generated inspiring relaxation activity. In said example, each user may take differing activities but, in the context that a State or plurality of States indicating successful completion of that activity, may result in same or similar positive State feedbacks in each subject's Life Context Graph.

In instances where resultant State feedbacks indicate subject States in need of further adjustment or intervention, a user may be able to perform necessary interactive intervention through the creation of new flows. Using the prior example, a subject failing to perform the suggested activity for several iterations of the suggestion may indicate a problem with the suggested activity, resulting in a new, user-defined flow such as suggesting a different activity determined to be beneficial to the behavioral health of the user; for example, a flow may suggest a different activity for the subject more known to generate the desired result, or a flow may suggest that the subject create a lifestyle pattern that allows for the performance of the originally suggested activity. More specifically, where the Life Context Graph indicates via States that it is a sunny day for the subject and the subject is at an elevated risk for depression and obesity, a flow may generate a message to the subject inspiring them to go for a run. If the subject fails to go for a run repeatedly, in turn generating States whereby a subject "did not go for a run," a flow may generate a message suggesting the user create a workout routine to schedule running. Alternatively, the flow may generate a message asking the subject why the subject did not go for a run, thereby creating additional State data via the subject's response (e.g. "knee hurts," "uncomfortably hot," "doesn't enjoy running," etc.).

Accordingly, in an embodiment of an invention as disclosed herein, a cloud-based system and method are provided for predictive modeling and positive adjustment of behavioral health. The system includes sensors collecting data associated with subject location and activity, and linked to a subject computing device. The system translates data aggregated from the data sources into state information, and iteratively updates, via the translated state information, a de-identified contextual model for the subject which in an embodiment may be a Life Context Graph as described herein. An end point server compares the de-identified contextual model to a de-identified aggregate of peer-based contextual models, wherein data security and privacy is preserved, and the system further iteratively updates the subject contextual model based thereon. The system accordingly identifies behavioral trigger actions based on the collected data and/or the updated subject contextual model, and generates a predetermined clinical response corresponding to the identified behavioral trigger action.

In one exemplary aspect of the aforementioned embodiment, the system may further include a clinician decision support interface configured for display and user interaction via a clinician computing device. The clinician decision support interface may comprise software tools enabling selective generation of a trigger comprising each of an IF or WHEN component, a state component and an action component, wherein a processor associated with the subject computing device is configured to identify the behavioral trigger action by identifying the presence of the state component via one or more of the collected data associated with subject activity and the updated subject contextual model, and causing implementation of the action component associated with the trigger.

In another exemplary aspect of the aforementioned embodiment, the state component may comprise a combination of one or more states developed from the translated data aggregated from the one or more data sources into state information.

In another exemplary aspect of the aforementioned embodiment, the action component may comprise one or more of an interactive messaging application executed via a graphical user interface associated with the subject computing device and an automated regulation of settings for one or more home environment devices associated with the subject.

In another exemplary aspect of the aforementioned embodiment, a processor associated with the subject computing device may further be configured to employ homomorphic encryption tools to de-identify the subject contextual model at one or more of the subject computing device and the end point server, and block chain signature tools to manage iterations or states associated with the contextual model.

In yet another exemplary aspect of the aforementioned embodiment, the data sources may comprise one or more remote state tracking devices linked to a hosted server and configured to provide one or more remote origins of state information, wherein the hosted server is configured to track a last known state of the state information when the remote state tracking device is not currently accessible via the communications network.

In still another exemplary aspect of the aforementioned embodiment, the system may further comprise a state feedback loop wherein the processor associated with the subject computing device is further configured to generate iterative updates to the contextual model based on subject action or inaction corresponding to the clinical behavioral response.

In still another exemplary aspect of the aforementioned embodiment, the processor associated with the subject computing device may further be configured to generate, responsive to subject inaction associated with the state feedback loop, one or more of a predetermined secondary clinical behavioral response and an interactive query string via a user interface for the subject computing device.

DETAILED DESCRIPTION OF THE INVENTION

Figure 1:
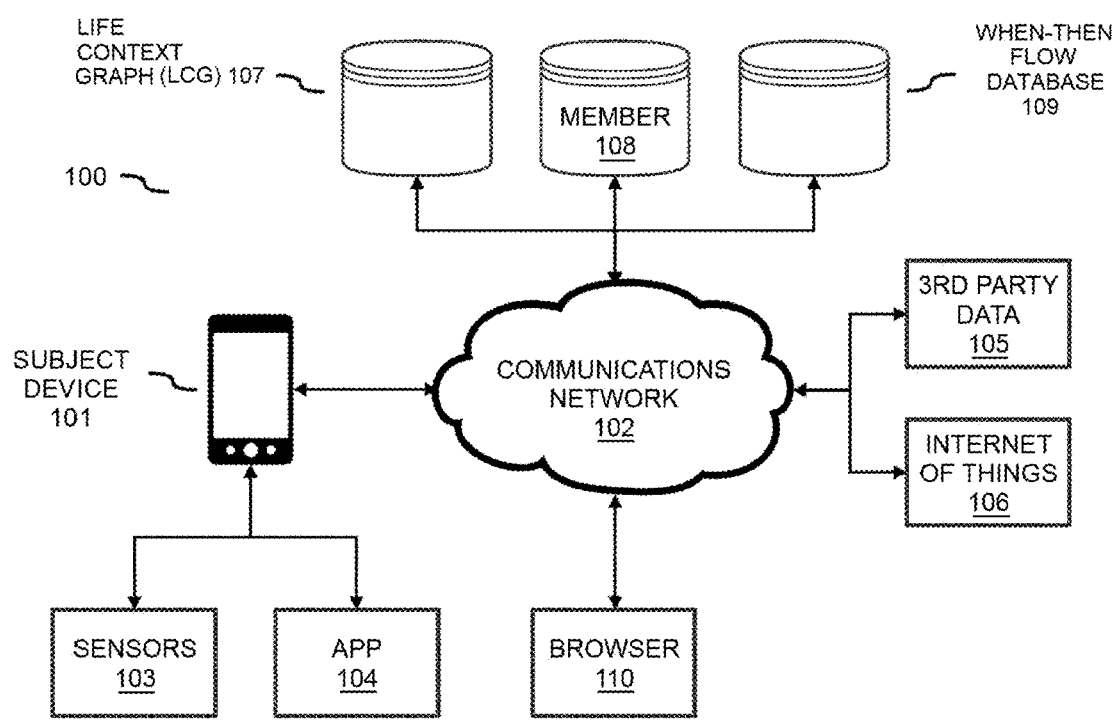
FIG. 1 is a block diagram representing an embodiment of a system for predictive modeling and adjustment of behavioral health according to the present disclosure.

Referring generally to FIGS. 1-5, various exemplary embodiments of an invention may now be described in detail. Where the various figures may describe embodiments sharing various common elements and features with other embodiments, similar elements and features are given the same reference numerals and redundant description thereof may be omitted below.

Referring first to FIG. 1, an exemplary embodiment of a system 100 for predictive modeling and adjustment of behavioral health as disclosed herein may include a subject device 101 associated with a specific subject and connected to a communications network 102. In various embodiments, a plurality of subject devices associated with the same subject may be connected to the communications network 102 and may include various computer devices including mobile phone, smartphone, tablet, laptop, desktop, and the like. Residing on the memory of the subject device 101 is a software application 104 for the display of a conversational user interface for systemic interaction with the subject. In various embodiments, the application may further be configured to perform the functions of collecting and processing of data obtained from proximate or device-associated sensors 103; creating, maintaining, and processing of Life Context Graphs (LCGs) as described in exemplary methods below; and creating of historical and productive models as described in exemplary methods below. In alternative embodiments, the aforementioned methods may be performed by a host server or other computer device communicatively connected via the communications network 102. In still other embodiments, the aforementioned methods may be performed via a plurality of subject devices 101 and/or other connected computer devices in a cloud-based, distributed implementation of software and hardware.

In various embodiments, third-party data sources 105 may further be connected to the communications network 102 and may provide data for processing similar to the subject device sensors 103. Such data sources may include Internet accounts, social media accounts, and other networked repositories of information pertaining to the subject. In various embodiments, the system 100 may further comprised networked "Internet of Things" devices 106 in association with the subject, such as home automation devices, healthcare devices, activity trackers, Internet enabled car data, and the like.

The exemplary system 100 further comprises a database for the storage and ongoing maintenance of Life Context Graphs 107, a HIPAA-compliant secure membership repository database 108, and a WHEN-THEN Flow database 109.

The exemplary system 100 aggregates data received from the subject device's servers, third party data sources 105, Internet of Things devices 106, and the secure membership repository 108 and translates the data received into various States associated with the subject in accordance with software instructions stored upon the application 104, whether client-side as illustrated, host server-implemented, or cloud-based. These States are added to an ongoing Life Context Graph associated with the subject in the Life Context Graph database 107. The system 100 further processes the States of the subject's Life Context Graph in association with historical trends derived from the user's Life Context Graph and/or peer group or population Life Context Graphs for a plurality of like subjects and makes predictive determinations and risk assessments thereupon.

The system 100 further continuously compares the States, predictive determinations, and risk assessments against Flows stored in the WHEN-THEN Flow database 109 and, in the event of a triggered match, executes the instructions of the matched WHEN-THEN Flow. In various embodiments, the WHEN-THEN Flow may create a conversational message to be displayed via the application 104 on the subject device 101. In some embodiments, the WHEN-THEN Flow may trigger the population of a report or dashboard on a separate browser 110, such as that of a coach, counsel, sponsor, or associated consumer such as a family member. For example, various alert states or informatics may be reported via the browser 110, such as when a trigger requests the review of a coach, counselor, sponsor, or other human expert.

The system 100 may perform the various functions continuously and receive information from the subject application, such as conversational input. The system 100 may be further configured to take subject-input information and process that information via natural language processing into State information. The crux of the system 100 is that the aggregation of data from the various input sources into State form, the updating of States into an ongoing Life Context Graph, the processing of the subject's Life Context Graph in association with the same or other Life Context Graphs, the reference and execution of IF-THEN Flows for the generation of at least message actions, and the translation of response actions and outputs into State inputs added to the Life Context Graph is performed continuously, such that the Life Context Graph is always evolving. In various embodiments, the system 100 may be further configured to perform machine learning functions such as adjusting the variables and algorithms of the application 104 in response to analytics performed on the Life Context Graph and execution of WHEN-THEN Flows, so as to increase the accuracy of predictive capability and ultimately improve positive contributions for adjusting behavior in the context of subjects' health and wellness.

Figure 2:
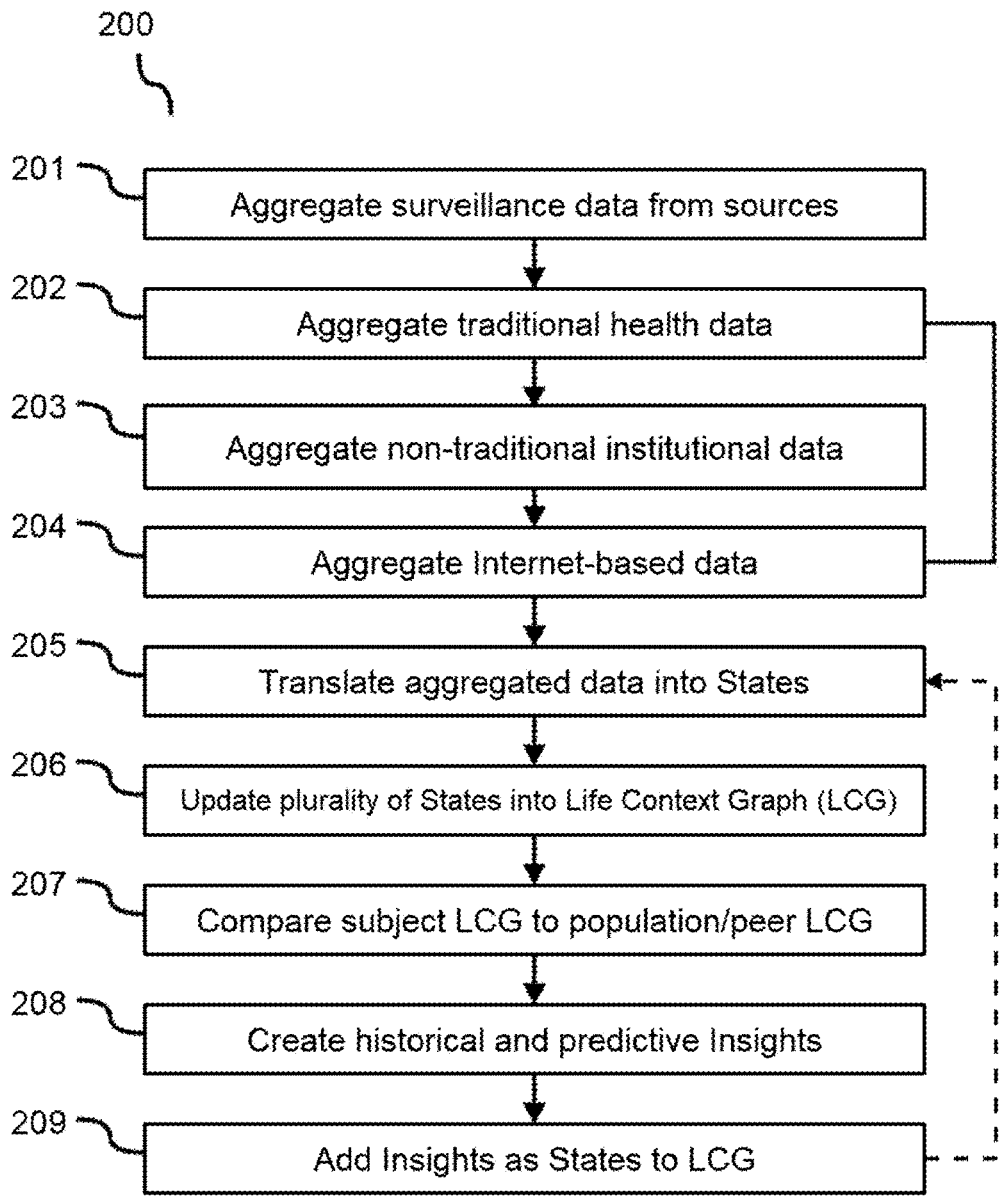
FIG. 2 is a flow diagram representing an embodiment of a process for aggregating surveillance data into a Life Context Graph as implemented by the system of FIG. 1.

Referring next to FIG. 2, an exemplary method 200 as disclosed herein for aggregating surveillance data into a Life Context Graph may be described in part or in whole as follows. The method 200 may begin at a first step 201 wherein the system aggregates various surveillance data pertaining to a subject. The first step 201 may comprise a series of aggregated sub-steps including the collection of traditional health data pertaining to the subject (202); the collection of non-traditional institutional data pertaining to the subject (203); and the collection of Internet-based data pertaining to the subject (204). Traditional health data may include, for example, health claims, pharmacy usage, lab data, biometric data, wellness data, and other health inputs traditionally collected by healthcare and wellness platforms. This health data may be further aggregated with non-traditional data including, for example, employment personnel information, employment administration data, performance reviews, benefit status changes, and other non-employment record information pertaining to a subject and available for data input. Such information may be integrated regardless of source, such that information may be automatically uploaded from Internet-based sources or may be manually input, such as in the case of records stored in hard-copy format.

Traditional and non-traditional data may be aggregated with Internet-based data including "Internet of Things" data and data obtained from subject-related connected devices. For example, the system may obtain available information from a subject's social media accounts including social media metadata, social media data, microblogging, user posts, pictures, moods, etc.; from phone sensors and lifestyle/activity tracking sensors for light, motion, exercise, sleep, heartrate, perspiration, blood sugar, etc.; from application data including application activity, user preferences, user activity, etc.; from home automation platforms including geofencing activity, light activation, motion activation, temperature, etc.; and other such data as can be obtained about subjects via devices connected via a communications network.

In an embodiment, each origin of a quantum of surveillance data ingested may be defined as a "Thing," wherein each "Thing" has a "Thing Shadow" on a cloud server for tracking the last known state of the Thing where the data origin for the Thing is not currently accessible via the communications network.

Traditional data, non-traditional data, and Internet-based data may pertain directly or indirectly to a subject and may pertain to more than one subject. For example, data pertaining to a subject's spouse, where the spouse has opted in to the system, may be associated with the subject for subsequent determination of the subject's States.

Upon aggregation of surveillance data, the system continues in step 205 by translating the collected data into informational component States. For example, the system may take surveillance data inputs including: healthcare and physical therapy information indicating knee injury; geolocational information about the subject's presence in Aspen, Colo.; social media pictures of a subject tagged wherein the subject is identified via photographic processing as engaging in the act of skiing; natural language analysis of social media microblogging indicating the subject's cognitive mood; work calendar information indicating time off work; proximity information indicating physical nearness to spouse and children; and activity tracking data indicating high rates of activity; and create one or more States therefrom by comparing the perceived activity or subject state to available keys and values. In the above example, various States could be generated including, "subject is on vacation," "subject is happy," "subject is with family," "subject is skiing," "subject is at high risk of exacerbating knee injury," "subject location is cold," "subject family is smiling," and so forth. States may in some embodiments be correlated directly with each surveilled quantum of data. In other embodiments, States may be determined from an amalgamation of data. For example, an empty work calendar, e-mail alert set, and recent purchase of plane tickets may result in a determinative State of subject being on vacation. States may be relative or indefinite, such as if "subject appears to be on vacation" or "subject appears to be happy." In some embodiments, States may be assemblies of complex keys and values, such as, "subject is on vacation with family in Aspen, Colo."

In an embodiment, States may in turn be defined as Things with Thing Shadows, wherein States not currently accessible or determinable may have a stored value as a Thing Shadow of the last defined State. Accordingly, States may be updated over time when one or more values for a key change. States may further be time-based, such that one State embodies a current value (e.g. subject is sleeping at 12:00 a.m.) and a similar State of the same key type embodies a different value (e.g. subject was awake at 11:59 p.m.). The process may be iterative, such that a State key has several values recorded over time, each stored as a separate State with timestamp.

In step 206, the system combines the plurality of generated states into a Life Context Graph. The Life Context Graph may represent an ongoing and collection of States pertaining to the subject and may be iterative, wherein the addition of new data is cumulative. In various embodiments, the Life Context Graph may be a combination of States and non-State subject data. In various embodiments, States within the Life Context Graph may be synthesized in aggregate, with each State receiving a time stamp such that the Life Context Graph represents an ongoing and dynamic picture of the subject's life experiences and behaviors. For example, for a given subject "Guy" may contain in part a collection of States, such as "Guy is currently walking around the ground floor of his home;" "Guy is working from home today;" "Guy is feeling joy;" "The time is a normal waking hour;" "Guy is in Behavioral Health Risk Segment 0 with a 30% risk of moving to Segment 1 and a 0.01% risk of moving to Segment 4 within the next 6 months based on all known information;" "Guy is in the proximity of his spouse and children who are also registered subjects." States may be concurrent or iterative. States may be recorded with a timestamp to provide a chronological timeline for the Life Context Graph.

In step 207, the system compares the data and States of the Life Context Graph for an individual subject with aggregated data and States for one or more Life Context Graphs associated with peer groups and/or populations to determine model variations therefrom. In an embodiment, the peer group or population Life Context Graph may be an aggregated set of Life Context Graphs for a plurality of other subjects delimited to certain thresholds; for example, where a subject has chronic arthritis, that subject may be compared to a peer group of other subjects suffering chronic arthritis. Comparative peer groups or populations may be plural, such that a subject's Life Context Graph is compared to the top 5% of at-risk individuals, the top 10% of at-risk individuals, males aged 30-35, New York City residents, etc.

In various embodiments, the data comparison step between the individual subject Life Context Graph and the aggregated Life Context Graph may employ differential privacy and homomorphic encryption, as well as other general encryption models, to transmit the subject's Life Context data (i.e. data and States) to an end-point aggregator, whereby the aggregator performs one or more statistical, logic-based analyses to compare the subject's Life Context data to the aggregate Life Context Graph for the population or peer group. In embodiments using homomorphic encryption, this comparison may be performed without decrypting or identifying the specific data pertinent to each subject as part of the population or peer group, thereby eliminating the risk of data breach via the aggregator's access to a full population schema of Life Context data; the population or peer group data is de-identified to allow comparison of the specific subject data to aggregate data for the peer group or population, thereby resulting in the same assessment whether raw, identified population data is available or not.

In one embodiment, the one or more assessments determined from comparative analysis of the Life Context Graphs are added as one or more nodes to the individual subject's Life Context Graph, creating a subsequent iteration of the subject's Life Context Graph for future performance of the same method 200.

Continuing now in step 208, the system performs historical and predictive modeling through statistical analysis of States within the Life Context Graph of the individual and of determinedly similar peer groups and/or populations. In an embodiment, assessment of current individual behavior and predictive modeling thereof is performed using common Baysean probability to assess current behavior exhibited in the context of past behavior. Other common statistical algorithms may be used to determine a change in risk context based on prior behaviors of the individual and comparative peer groups and populations, wherein deviation from a predicted norm in the form of change in State may increase the predictive model regarding one or more categories of risk. For example, statistical models may further include Coarsened Exact Matching or similar techniques for comparing a subject to other subjects for sponsor, demographics, health history, and the like, as well as assignment of the subject to a delineated behavioral health segment based on severity and risk of current and future conditions.

Determinations of risk state based on comparison of past and predictive models may be categorized as Insights. For example, where modeling of States within an individual subject's Life Context Graph by comparison to a peer group of similarly aged and able individuals suggest that the individual may be declining in health and mobility far more rapidly, the system may categorize as an Insight that the subject risks a tripling of total cost of living within the next five years.

In step 209, the system updates the Life Context Graph with the Insight information derived in step 208, wherein the Insights are translated into States and added back to the Life Context Graph for the subject. Accordingly, translation of Insights into States that are added back into the Life Context Graphs allows future iterations of the method 200 to utilize the Insights derived, enabling the system to self-learn and improve predictive analysis through regressive analysis of prior States. Using the previous paragraph's example, the system can determine in an iteration five years later whether the cost of living for the subject has indeed tripled and verify if the initial prediction was correct. In certain embodiments, the system may adjust the predictive Insight variables to allow for more accurate determination of risks. In some embodiments, the system may adjust the selection of peer groups based upon the verified accuracy of prior Insights. In this manner, the system may, for example, identify that pregnant women respond differently to a pattern of messages than non-pregnant women and, in future iterations of the method 200, select for a pregnant subject a peer group of only pregnant subjects as opposed to the whole population of women.

Figure 3:
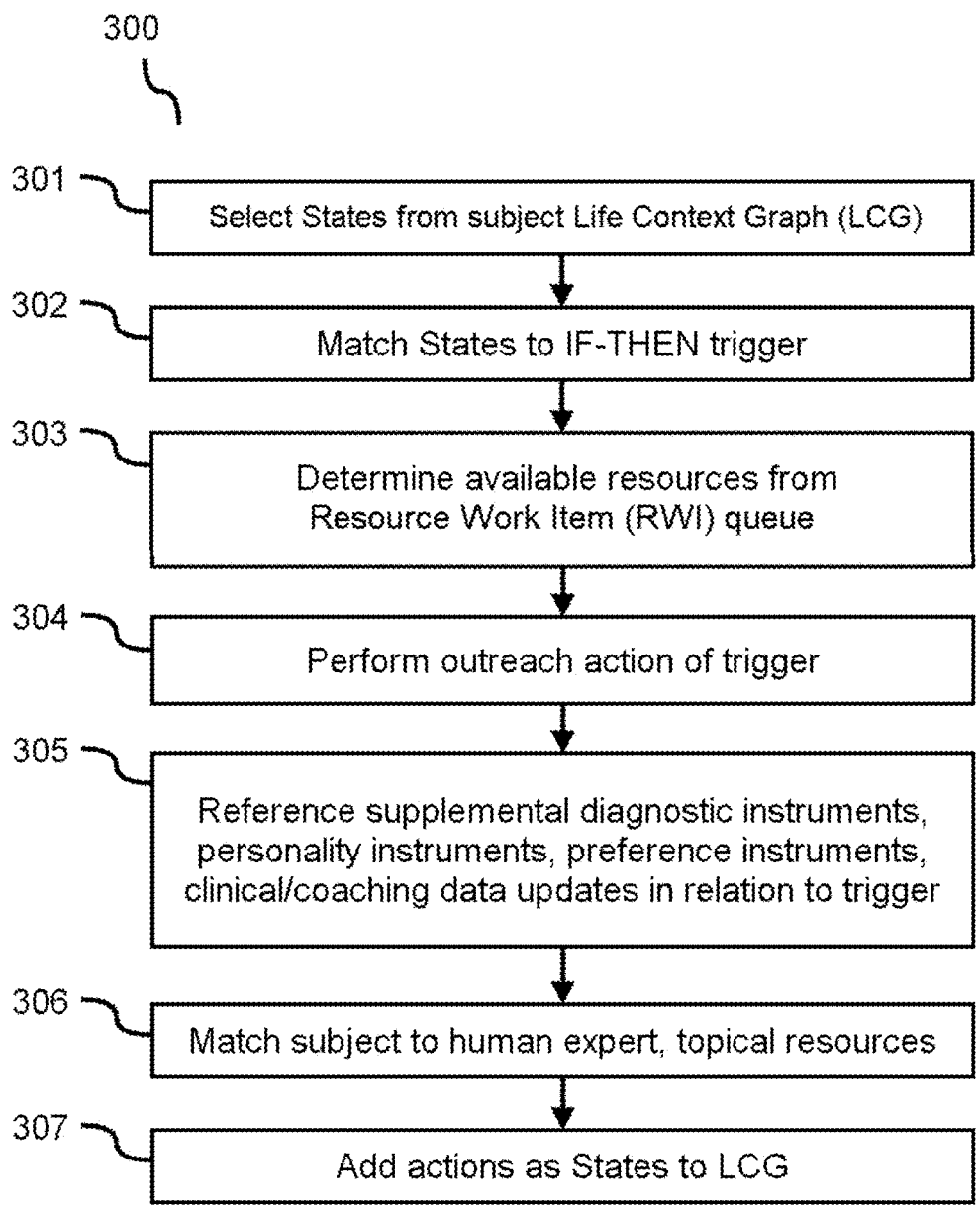
FIG. 3 is a flow diagram representing an embodiment of a process for matching an individual subject to health resources based upon analytics derived from the subject's Life Context Graph as implemented by the system of FIG. 1.

Referring next to FIG. 3, an exemplary method 300 as disclosed herein for matching an individual subject to health resources based upon analytics derived from the subject's Life Context Graph may be described in part or in whole as follows. The method 300 begins at a first step 301 where the system identifies and selects a plurality of States from a subject's Life Context Graph. The identification and selection may be algorithmically determined based upon prior programming where the existence of a certain set of States indicates a grouping of States to be selected.

The system then, in step 302, matches the selected States to a predetermined trigger action. In an embodiment, the trigger action may be expressed as visual programming in the form of IF-THEN trigger, (a.k.a. logical blocks, Flows, recipes, actions). The States may be matched to the IF component of the trigger. For example, a combination of States of "It is morning;" "subject is now awake;" "last night the house temperature was 78 degrees Fahrenheit;" "subject awoke three times last night;" and "subject tossed and turned during sleep" might match an IF-THEN trigger to send the subject a message stating, "Good morning. It looks like you didn't sleep very well. Are you tired?" In certain embodiments, IF-THEN triggers may be matched based upon subject responses which may in further embodiments be expressed in the form of additional States added to the Life Context Graph. For example, receiving the response, "Yes, I'm tired," may be filtered through a natural language processing engine to indicate a response in the affirmative, generating a new State added to the Life Context Graph as "subject is tired." This new State may in turn be matched with other States either individual or separate to the prior iteration, such as particularly "last night the house temperature was 78 degrees Fahrenheit," to generate an exemplary IF-THEN action to send a message, "It looks like your house was really hot last night (78 degrees Fahrenheit). You might sleep better tonight if you turn down the temperature, but consider taking a nap if you can."

In certain embodiments, the system may perform step 303 wherein the system references a Resource Work Item (RWI) queue wherein the Resource Work Item represents an intervention for a subject that can be performed by a resource such as, for example, a coach or clinician, and then determines an appropriate trigger action or further modified the match of step 302 based upon the availability of resources and state of Resource Work Item queues. The primary purpose of this step is to manage the workload of resources such as coaches and counselors by load-balancing the work across them. For example, if a trigger action for step 302 is determined to be "meet with physical therapist weekly for Achilles tendon rupture recovery for a duration of six months," the Resource Work Item would be a physical therapy meeting, and the resource would be a licensed therapist within the geographic vicinity of the patient and capable of performing Achilles tendon rupture rehabilitation. The system may determine in this example that there are seven physical therapists within the geographic area capable of performing the Work Resource Item. Of these seven resources, four have 25+ other commitments in queue, two have 10+ commitments in queue, and one has only five commitments in queue. The system may determine that the therapist with only five commitments in queue is the best resource to be associated with the trigger action as a matter of load balancing. However, the load balancing may consider other factors beyond queue items, such as specialization and expertise, proximity to subject, efficiency of work performed, satisfaction ratings, effectiveness, etc.

In step 304, the system determines and performs the action of the trigger (i.e. the THEN component). In exemplary embodiments, the outreach action may take the form of various messages to be delivered to the subject via an application on the subject's mobile device. In other embodiments, the outreach action may take the form of software instructions to be sent to various peripheral devices connected to the communications network in association with the subject. For example, the system may adjust the temperature of an Internet-connected thermostat in the subject's house or hospital room.

In step 305, the system may optionally reference supplemental diagnostic instruments, personality instruments, preference instruments, and clinical/coaching data updates available in relation to the IF-THEN trigger selected. For example, if an IF-THEN trigger cues for a subject who has indicated repeated nights of restlessness and lack of sleep, additional resources may be referenced for chronic fatigue and insomnia. In some embodiments, additional IF-THEN triggers or diagnostic action may be taken in accordance with information gleaned therefrom, such as if the additional data referenced is in the form of IF-THEN triggers. In some embodiments, the system may generate IF-THEN triggers based on natural language processing of the supplemental instruments or clinical/coaching data.

The system may further perform step 306 wherein the system matches the subject to one or more available prescribed resources such as community or digital resources or a human expert. For example, continuing the previous example of restlessness and insomnia, the system may send the State data of the subject's Life Context Graph to a selected sleep expert. The selection of additional resources or a human expert may be made based upon States or data not a part of the original trigger. For example, the system may select a sleep expert based on proximity to the subject, the subject's healthcare plan coverage, the severity of the sleep deprivation, etc. In some embodiments, the prescribed resource matched may further be associated with prescription parameters such as frequency, intensity, duration, and the like. For example, the prescribed resource "coaching" may be associated with an intensity parameter and duration parameter, such that a match to "coaching" may be further categorized as a match to "coaching for 12 weeks at high intensity." Prescribed matches may be iterative, such that the prescription "coaching for 12 weeks at high intensity" may further be matched with "then 12 weeks' maintenance" and "then 1 year's surveillance."

In various embodiments, step 306 may further involve the performance of intervention of the prescribed resources. For example, for a matched prescribed resource of "patient-counselor sessions performed weekly" may further involve the scheduling of said weekly sessions between patient and counselor. As another example, a prescription of outbound messages sent via WHEN-THEN automation functions may be sent by the system.

In step 307, the performed IF-THEN triggers and actions of the previous steps may be translated into State data and added back to the subject's Life Context Graph for future iterations of the methods 200 and 300.

Figure 4:
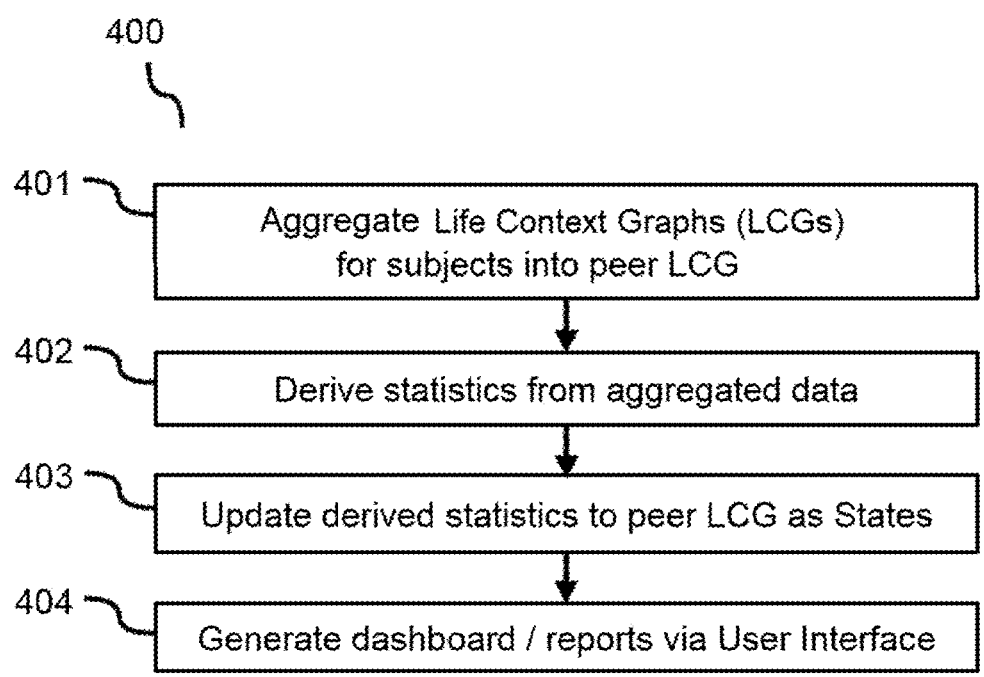
FIG. 4 is a flow diagram representing an embodiment of a process for generating reports for statistical comparisons of a subject's wellness data and States to the wellness data and states of one or more peer groups and/or populations as implemented by the system of FIG. 1.

Referring next to FIG. 4, an exemplary method 400 as disclosed herein for generating reports for statistical comparisons of a subject's wellness data and States to the wellness data and states of one or more peer groups and/or populations may be described in part or in whole as follows. The method 400 at step 401 wherein subjects are grouped as a peer group or population and the Life Context Graphs of each representative subject are aggregated. Subjects may be grouped according to user preference, such as the case of manual selection of criteria, or in some embodiments subjects may be grouped by heuristic determination of the system, such as where the system identifies commonality of traits between subjects' States. Groupings may in some embodiments be expressed as organization or entity context graphs associated with a sponsoring entity such as an employer or practice group, health plan, affinity group, and the like. Subjects grouped may be associated with the organization or entity, wherein one or more context graphs are aggregated therefrom. For example, the system may aggregate for a manufacturing employer subjects based upon employment location or factory location.

In step 402, the system derives population- or peer-group-level statistics from the aggregated Life Context Graph information of the selected subjects. Exemplary statistics include but are not limited to Intent to Stay (the percentage of subjects likely to stay in current employment or school), Balanced Response (the percentage of individuals indicating a balanced response to a potential destabilizing stimulus or traumatic event), Location Category Heat Map (heat map demonstrating subject location at various categories of time such as before/during/after work), User Engagement Level, and Net Promoter Score.

In step 403, the statistics derived are updated into a Life Context Graph for the peer group, wherein the States and data are de-identified and/or anonymized with reference to the individual subjects contributing the underlying data but relevant to the overall population or peer group. For example, whereas an individual subject's Life Context Graph may contain the State, "subject ran for 4.6 miles today," a peer group Life Context graph may aggregate that State with a plurality of other, similar States to create a population State of, "473 subjects ran a median of 4.5 miles today, mean 3.2 miles, Q1 1.4, Q3 7.6, total range of 0.0 to 13.2 miles for the population." Such State may be expressed as a single complex State or multiple simple States, wherein comparison of any individual subject's similar running statistic for the same time period may be compared against the anonymized or de-identified population model to determine relative placement of the subject's running State in comparison to the model population. In step 404, the system may generate dashboards and reports via a user interface in reference to the population Life Context Graph and individual subject's Life Context Graph. In certain embodiments, the dashboard will display alerts for an individual where historical or predictive assessment indicate high risk or an item actionable by a human expert or the subject. Such reports may be useful for an individual subject to identify high risk areas in need of attention for improving personal health and wellness. Reports may further be useful to health and wellness professionals monitoring an individual or a population group for determining trends and patterns of wellness risk and active response.

In an embodiment, method 400, individually or in combination with methods 200 and 300 may incorporate machine learning, human learning, or a combination thereof. The system may in the context of this step and the overall method identify which trigger actions result in the most positive changes and sustained levels of desired outcomes for the lowest comparative cost. For example, the system might observe that certain trigger actions such as messaging actions are most effective when sent a certain time after a determined event for working-age population, but are most effective when sent immediately after the determined event for pre-working age population. The system may, in the process of deriving WHEN-THEN trigger actions and in updating derived statistics as States, shift underlying variables of the determination algorithms to favor the more effective action for a subject based upon peering and effectiveness of outcome. In an embodiment, algorithms may be pre-programmed or programmed by human action, such as via the WHEN-THEN interface, based on correlation of cause and effect. In another embodiment, algorithms may be based on supervised neural networks where the root mechanism is unknown but the lowest cost intervention for a trigger action to achieve the desired result is known. In yet another embodiment, algorithms may be based on unsupervised neural networks where the root mechanism is unknown but the lowest cost intervention trigger action to achieve the desired result is still known. In an embodiment, a combination of any one or more of the above three bases may be used.

The adjustment to the algorithms may be changed or modified in value so as to populate the user interface dashboard in method 400 with the most relevant data; to change matching parameters in method 300 so as to result in varying combinations of prescription parameters such as frequency, duration, intensity, etc.; to improve the aggregation of surveillance data through better curation of valuable data sources; and in some embodiments to change the modality and nature of engagement interactions such as messaging (for example, substituting the term "Hey" for "Hello" in outgoing messages where "Hey" consistently yields more desirable results for a subject or plurality of subjects).

Figure 5:
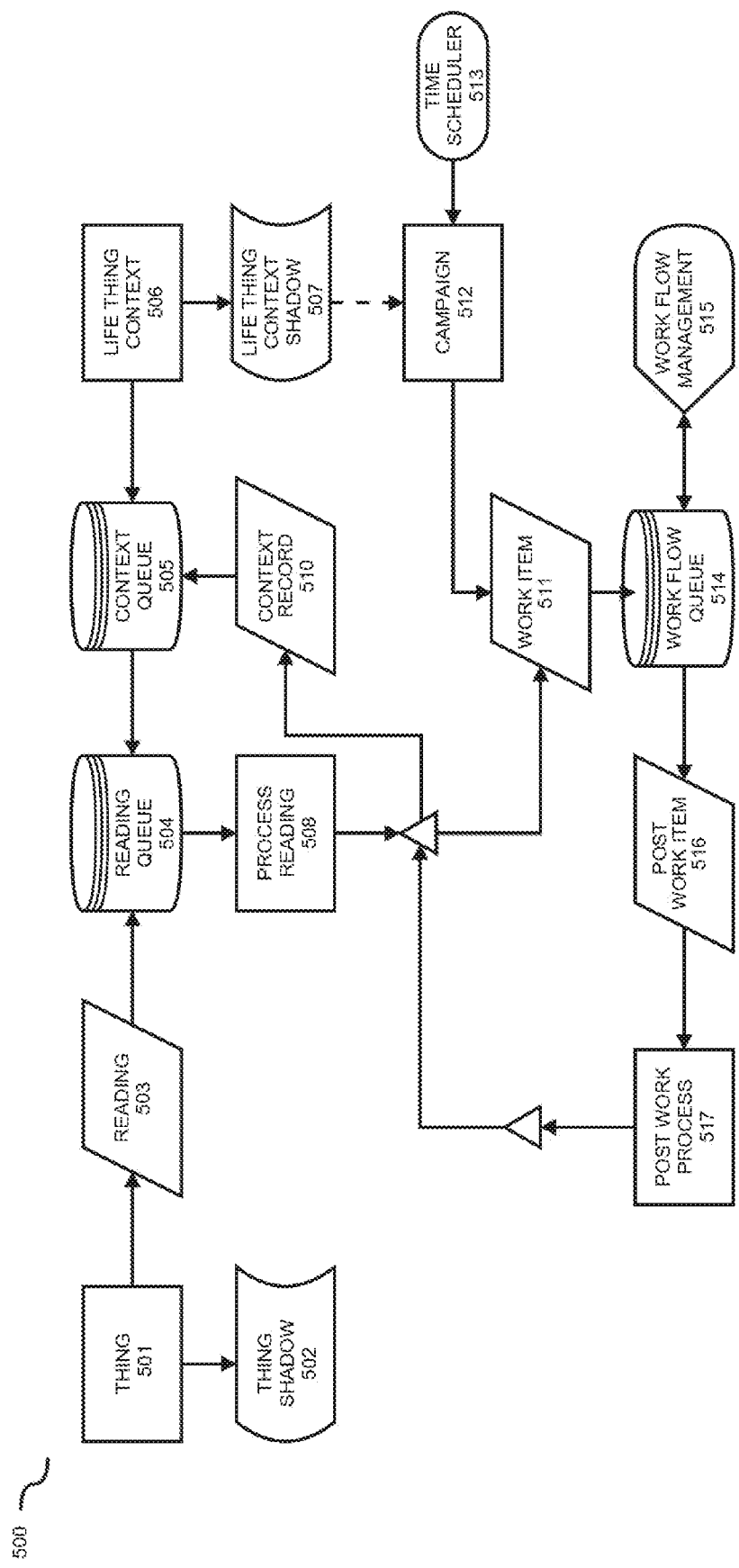
FIG. 5 is a flow diagram representing a second embodiment of a system for predictive modeling and adjustment of behavioral health according to the present disclosure.

Referring next to FIG. 5, another exemplary embodiment of a system 500 for predictive modeling and adjustment of behavioral health. The system 500 may include a Thing 501 and an associated Thing Shadow 502 which stores as data the last known state of the Thing 501. The system may read as a data input 503 the state of the Thing 501, or, where the Thing state is not presently available, retrieve the state of the associated Thing Shadow 502. The system may further store the reading of the data input 503 in a Reading Queue database 504 from which the Life Context Graph may be derived.

The system 500 may further comprise a Context Queue database 505 comprising context states of Things directly associated with a user (a "Life Thing") 506. The Life Thing 506 may in an embodiment be a set or subset of all Things 501, and in a further embodiment may be associated with a stored Life Thing Shadow 507 preserving the last known state of the Life Thing 506. The Life Things 506 or Life Thing Shadows 507 stored in the Context Queue database 505 may further be stored in, exported to, or expressed within or as the Reading Queue database 504.

The system 500 processes the stored data (e.g. readings 503 and Context Queue data from database 505) pursuant to WHEN-THEN or WHEN-DO methodology (508) and extracts additional context data 509. For example, the Reading Queue database 504 may have stored data such as a user's heart rate data indicating a resting heart rate, phone accelerometer data indicating no movement in 30 minutes, and Bluetooth proximity data indicating the user is in or near the living room. The system may process this data to extract a contextual state that the user is napping on the living room couch. This extracted data may be fed back into the context queue as a Context Record input 510, and/or the extracted context data may be forwarded as a Work Item input 511.

In various embodiments of system 500, one or more programmatic processes may be described as Campaigns 512. Campaigns 512 may in certain embodiments be intent-based and enacted in accordance with WHEN-THEN or WHEN-DO methodology. For example, a Campaign 512 may be a population health campaign wherein the schema and intent for the campaign is to engage in a healthier lifestyle, such as by motivating users to walk at least 8,500 steps per day. For further example, the Campaign 512 may be a process by which the system identifies users with suboptimal health states/contexts or health performance states/contexts and initiates a process for generating a message suggesting the user engage in healthier activities. In further embodiments, the Campaign 512 may initiate a process for querying for more Thing or Life Thing state and/or context information (e.g. asking a user how they are feeling).

The Campaign 512 may in an embodiment be run periodically in accordance with a Time Scheduler 513. The Time Scheduler 513 may dictate when the campaign 512 is run based upon static state data programmed by coaches, clinicians, and other behavioral health experts, or alternatively (or, in further embodiment, additionally) based upon effective states learned by the system 500 from multiple iterations of system 500's methods for achieving desired Thing state data.

The output of a campaign 512 may comprise one or more Work Item inputs 511. The Work Item inputs 511 may further be stored in a Work Flow Queue database 514, wherein the Work Flow Queue comprises a series of programmatic steps for one or more desired outcomes. In an embodiment, the Work Flow Queue items may be displayed to one or more behavioral health experts via a user interface 515 wherein the behavioral health expert can adjust the programmatic step relationships to improve the desired outcome. Conversely, the behavioral health expert may make no adjustments to the Work Flow Queue, or the system itself may self-adjust the Work Flow Queue to the best determined relationship model in accordance with prior iterations of the system 500 processes.

The Work Flow Queue items may be exported from the Work Flow Queue database 514 as Post Work Items 516. Post Work Items 516 may in respective embodiments be self-adjusted or user-adjusted programmatic step data wherein the step relationships are arranged to effect an improved outcome. The Post Work Items 516 may be further processed according to the WHEN-THEN or WHEN-DO methodology (the process 517), wherein a performance may be output as a data extraction 518 (e.g. a message, a context, a state, a datum, an entity, a relationship, or a work item). The extracted output may in various embodiments may in turn be fed back into the system 500 as a Context Record 510 or a Work Item 511, allowing the processes to repeat iteratively.

Depending on the embodiment, certain acts, events, or functions of any of the algorithms described herein can be performed in a different sequence, can be added, merged, or left out altogether (e.g., not all described acts or events are necessary for the practice of the algorithm). Moreover, in certain embodiments, acts or events can be performed concurrently, e.g., through multi-threaded processing, interrupt processing, or multiple processors or processor cores or on other parallel architectures, rather than sequentially.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable medium known in the art. An exemplary computer-readable medium can be coupled to the processor such that the processor can read information from, and write information to, the memory/storage medium. In the alternative, the medium can be integral to the processor. The processor and the medium can reside in an ASIC. The ASIC can reside in a user terminal. In the alternative, the processor and the medium can reside as discrete components in a user terminal.

The term "user interface" as used herein may unless otherwise stated include any input-output module with respect to the hosted server including but not limited to web portals, such as individual web pages or those collectively defining a hosted website, mobile applications, desktop applications, mobile applications, telephony interfaces such as interactive voice response (IVR), and the like. Such interfaces may in a broader sense include pop-ups or links to third party websites for the purpose of further accessing and/or integrating associated materials, data or program functions via the hosted system and in accordance with methods of the present invention.

The term "communications network" as used herein with respect to data communication between two or more parties or otherwise between communications network interfaces associated with two or more parties may refer to any one of, or a combination of any two or more of, telecommunications networks (whether wired, wireless, cellular or the like), a global network such as the Internet, local networks, network links, Internet Service Providers (ISP's), and intermediate communication interfaces.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The previous detailed description has been provided for the purposes of illustration and description. Thus, although there have been described particular embodiments of a new and useful invention, it is not intended that such references be construed as limitations upon the scope of this invention except as set forth in the following claims.

What is claimed is:

1. A system for predictive modeling and positive adjustment of behavioral health, the system comprising:
   one or more data sources comprising one or more sensors configured to collect data associated with subject location and activity;
   a subject computing device associated with at least the one or more sensors and linked to a communications network, and further comprising a processor configured to:
      translate data aggregated from the one or more data sources into state information,
      iteratively update, via the translated state information, a de-identified contextual model associated with a subject,
      transmit the de-identified contextual model to an end point server configured to compare the de-identified contextual model to a de-identified aggregate of one or more peer-based contextual models and further iteratively update the subject contextual model based on said comparison,
      identify a behavioral trigger action by the subject based on one or more of the collected data associated with subject activity and the updated subject contextual model, and provide an automated predetermined clinical response in association with the subject corresponding to the identified behavioral trigger action,
      predict one or more changes in the state information based on the one or more of the collected data associated with subject activity and the updated subject contextual model, and
      direct any one or more of an identified behavioral trigger action, a provided clinical response, and a predicted change in the state information to a clinician decision support interface configured for display and user interaction via a clinician computing device,
   wherein the clinician decision support interface comprises software tools enabling selective generation of customized flows comprising new behavioral trigger actions and corresponding automatic clinical responses.

2. The system of claim 1,
   wherein the clinician decision support interface comprises software tools enabling selective generation of a trigger comprising each of an IF or WHEN component, a state component and an action component,
   wherein the processor associated with the subject computing device is configured to identify the behavioral trigger action by:
      identifying a presence of the state component via one or more of the collected data associated with subject activity and the updated subject contextual model, and
      causing implementation of the action component associated with the trigger.

3. The system of claim 2, wherein the state component comprises a combination of one or more states developed from the translated data aggregated from the one or more data sources into state information.

4. The system of claim 2, wherein the action component comprises one or more of an interactive messaging application executed via a graphical user interface associated with the subject computing device and an automated regulation of settings for one or more home environment devices associated with the subject.

5. The system of claim 1, wherein the processor associated with the subject computing device is further configured to employ
   homomorphic encryption tools to de-identify the subject contextual model at one or more of the subject computing device and the end point server, and
   block chain signature tools to manage iterations or states associated with the contextual model.

6. The system of claim 1, wherein the data sources comprise one or more remote state tracking devices linked to a hosted server and configured to provide one or more remote origins of state information, wherein the hosted server is configured to track a last known state of the state information when the remote state tracking device is not currently accessible via the communications network.

7. The system of claim 1, further comprising a state feedback loop wherein the processor associated with the subject computing device is further configured to generate iterative updates to the contextual model based on subject action or inaction corresponding to the predetermined clinical response.

8. The system of claim 7, wherein the processor associated with the subject computing device is further configured to generate, responsive to subject inaction associated with the state feedback loop, one or more of a predetermined secondary clinical behavioral response and an interactive query string via a user interface for the subject computing device.

9. A method for predictive modeling and positive adjustment of behavioral health, the method comprising:
   continuously collecting and aggregating, via at least one or more sensors, data associated with subject location and activity;
   translating the aggregated data into state information;
   iteratively updating, via the translated state information, a de-identified contextual model associated with a subject;
   transmitting the de-identified contextual model to a centralized location via a communications network;
   comparing the de-identified contextual model to a de-identified aggregate of one or more peer-based contextual models;
   iteratively updating the subject contextual model based on said comparison;
   identifying a behavioral trigger action by the subject based on one or more of the collected data associated with subject activity and the updated subject contextual model, and providing an automated predetermined clinical response corresponding to the identified behavioral trigger action;
   predicting one or more changes in the state information based on the one or more of the collected data associated with subject activity and the updated subject contextual model; and
   directing any one or more of an identified behavioral trigger action, a provided clinical response, and a predicted change in the state information to a clinician decision support interface configured for display and user interaction via a clinician computing device,
   wherein the clinician decision support interface comprises software tools enabling selective generation of customized flows comprising new behavioral trigger actions and corresponding automatic clinical responses.

10. The method of claim 9, further comprising:
enabling, via the clinician decision support interface, selective generation of a trigger comprising each of an IF or WHEN component, a state component and an action component; and
identifying the behavioral trigger action by:
identifying a presence of the state component via one or more of the collected data associated with subject activity and the updated subject contextual model, and
causing implementation of the action component associated with the trigger.

11. The method of claim 10, wherein the state component comprises a combination of one or more states developed from the translated data into state information.

12. The method of claim 10, wherein the action component comprises an interactive messaging application executed via a graphical user interface associated with a subject computing device.

13. The method of claim 10, wherein the action component comprises an automated regulation of settings for one or more home environment devices associated with the subject.

14. The method of claim 10, further comprising:
employing homomorphic encryption tools to de-identify the subject contextual model at one or more of the subject computing device and an end point server, and employing block chain signature tools to manage iterations or states associated with the contextual model.

15. The method of claim 14, further comprising generating iterative updates to the contextual model based on subject action or inaction corresponding to the predetermined clinical response.

16. The method of claim 14, further comprising generating, responsive to subject inaction, one or more of a predetermined secondary clinical behavioral response and an interactive query string via a user interface for the subject computing device.

17. A system for predictive modeling and positive adjustment of behavioral health, the system comprising:
means for aggregating data about a subject from a plurality of connected devices;
means for continuously translating the aggregated data into an ongoing series of states defining a Life Context Graph;
means for comparing the Life Context Graph to a de-identified aggregate of one or more peer-based Life Context Graphs;
means for predicting potential behavioral health risks for the subject; and
means for providing automated queries and messages to the subject with respect to behavioral health improvements and adjustments corresponding to the predicted potential risks.

18. The system of claim 17, wherein the means for comparing the Life Context Graph to a de-identified aggregate of one or more peer-based Life Context Graphs comprises employing differential privacy and homomorphic encryption models to transmit the subject's aggregated data and states to an end-point aggregator.

19. The system of claim 18, further comprising means for ensuring authenticity of data in untrusted networks across graph iterations or states.

20. The system of claim 17, wherein the means for generating automated queries and messages further comprises asynchronous program execution for generation of a linear workflow with respect to trigger designation and specified actions.

* * * * *